(12) United States Patent
Tanimoto

(10) Patent No.: US 8,530,549 B2
(45) Date of Patent: Sep. 10, 2013

(54) RUBBER CRAWLER

(75) Inventor: Yoshikazu Tanimoto, Yokohama (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 13/380,765

(22) PCT Filed: Jun. 25, 2010

(86) PCT No.: PCT/JP2010/004247
§ 371 (c)(1),
(2), (4) Date: Dec. 23, 2011

(87) PCT Pub. No.: WO2010/150557
PCT Pub. Date: Dec. 29, 2010

(65) Prior Publication Data
US 2012/0108738 A1 May 3, 2012

(30) Foreign Application Priority Data
Jun. 26, 2009 (JP) ................. 2009-152007

(51) Int. Cl.
*C08K 3/10* (2006.01)
*C08K 5/45* (2006.01)

(52) U.S. Cl.
USPC ........................... 524/84; 524/435

(58) Field of Classification Search
USPC ................. 524/84, 435
See application file for complete search history.

(56) References Cited

U.S. PATENT DOCUMENTS 6,296,329 B1   10/2001   Rodgers et al.
8,148,452 B2 *   4/2012   Miyazaki ................. 524/84

FOREIGN PATENT DOCUMENTS

| CN | 101314652 A | 3/2008 |
| EP | 0 677 546 A1 | 10/1995 |
| JP | 5-163398 A | 6/1993 |
| JP | 7-286049 A | 10/1995 |
| JP | 2001-26671 A | 1/2001 |
| JP | 2002-30186 A | 1/2002 |
| JP | 2005-139082 A | 6/2005 |
| JP | 2005-139239 A | 6/2005 |
| JP | 2005-335611 A | 12/2005 |

OTHER PUBLICATIONS

Chinese Office Action for corresponding Application No. 201080028110.9 issued Jul. 9, 2013, English translation.

* cited by examiner

*Primary Examiner* — Kriellion Sanders
(74) *Attorney, Agent, or Firm* — Sughrue Mion, PLLC

(57) ABSTRACT

The present invention provides a rubber crawler with high durability by using the rubber composition, wherein said rubber composition exhibits enhanced adherence between rubber and metal reinforcing material, such as steel cord and the like, particularly adherence after heat aging and under high humidity, without using vulcanizing retarder, such as CTP, which has possibility of generating problems, such as blooming and lowering rubber physical properties after vulcanization; using vulcanization accelerator having the adequate vulcanization retarding effect exerting excellent working ability; lowering rubber scorching as much as possible. The rubber crawler of the present invention comprises a rubber composition as the treatment rubber thereof, which comprises in the amount of 0.1 to 10 parts by weight of sulfenamide-containing vulcanization accelerator, 0.03 to 3 parts by weight of cobalt-containing composition as the equivalent amount of cobalt and 0.3 to 10 parts by weight of sulfur, relative to 100 parts by weight of rubber component.

[Formula 1]

(I)

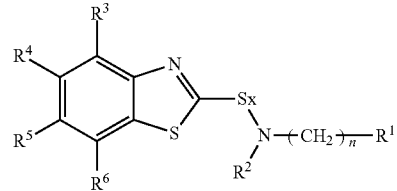

5 Claims, 1 Drawing Sheet

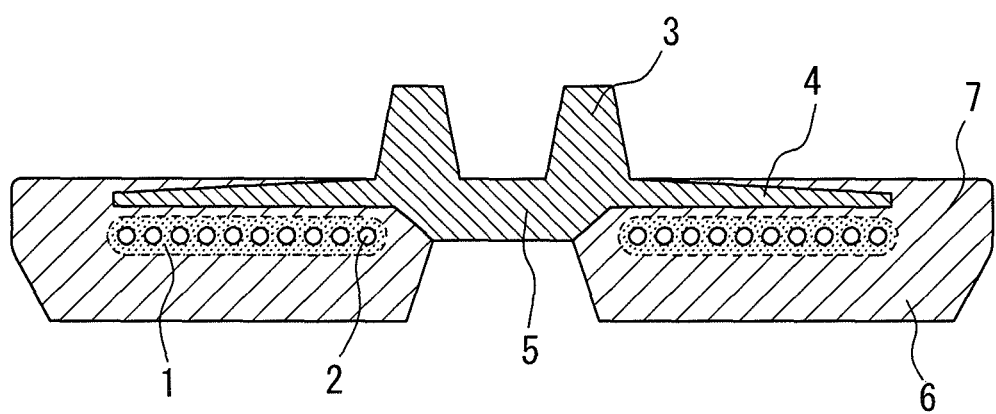

RUBBER CRAWLER

CROSS REFERENCE TO RELATED APPLICATIONS

This application is a National Stage of International Application No. PCT/JP2010/004247 filed on Jun. 25, 2010, which claims priority from Japanese Patent Application No. 2009-152007, filed on Jun. 26, 2009, the contents of all of which are incorporated herein by reference in their entirety.

TECHNICAL FIELD

The present invention relates to a rubber crawler using rubber composition having excellent adhesion durability, comprising a certain sulfenamide-containing vulcanization accelerator, as the treatment rubber.

RELATED ART

Currently, rubber crawlers are used for traveling section of machineries used in agriculture, construction, and the like. Such rubber crawlers require strength sustainable in severe environment of usage, so composite materials having metal reinforcing material, such as steel cord coated with treatment rubber (rubber-metal reinforcing material) are utilized in order to increase reinforcement and durability of the rubber by such metal reinforcing material.

For producing these rubber-metal reinforcing material, when the rubber and the metal adhere each other, a method for simultaneously bonding rubber-to-metal and rubber-to-rubber i.e. direct vulcanization adhesion method, is known. In this case, it is considered effective to use a sulfenamide-containing vulcanization accelerator which provides slow-acting property to the vulcanization reaction, when vulcanization of rubber and bonding of rubber to metal are carried out at the same time. A commercially available sulfenamide-containing vulcanization accelerator includes, for example, N,N'-dicyclohexyl-2-benzothiazolesulfenamide (hereinafter abbreviated as "DCBS"). Further, when slow-acting property is required, vulcanization retarder, such as N-(cyclohexylthio)phthalimide (hereinafter abbreviated as "CTP"), is also combined with sulfenamide-containing vulcanization accelerator. Moreover, sulfenamide-containing vulcanization accelerator besides the above DCBS, such as bissulfenamide accelerator represented by a certain formula (refer to patent reference 1) and benzothiazolesulfenamide-containing vulcanization accelerator derived from natural fat and oil (refer to patent reference 2), are known.

Despite the above, the natural rubber is frequently used as a major part for the rubber component in the rubber composition for use in the treatment rubber of the rubber crawler. In the above mentioned case, sulfenamide-containing vulcanization accelerator, such as DCBS, has high possibility of extremely slowing the vulcanization speed, so the sulfenamide-containing vulcanization accelerator, such as N-cyclohexyl-2-benzothiazolesulfenamide (hereinafter abbreviated as "CBS") and N-t-butylbenzothiazole-2-sulfenamide (hereinafter abbreviated as "TBBS") are preferably used.

PRIOR ARTS

Patent References

Ref. 1 JP2005-139082
Ref. 2 JP2005-139239

DISCLOSURE OF THE INVENTION

Problems to be Solved by the Invention

However, when prior vulcanization accelerator, such as CBS and TBBS are used, there is possibility of proceeding vulcanization reaction before completion of adhesion reaction between rubber and metal reinforcing material, thus there may be a case in which sufficient adherence cannot be obtained with these reinforcing material. In addition, it is considered that when current vulcanization accelerator is used, kneading operation tends not be able to attain favorable condition due to increase in Mooney viscosity more than the necessary level, and also it is difficult to ensure favorable Mooney scorch time simultaneously with favorable condition of vulcanizing acceleration. Furthermore, when the above vulcanization retarder is combined with the current vulcanization accelerator, such combination may generate problems of adverse effects to the physical properties of the rubber, and cause blooming which exerts adverse effects to appearance and adherence of the vulcanized rubber, depending on the quantity compounded.

Additionally, in a general production of the rubber crawler, it is required to produce a sheet-like rubber-metal reinforcing material in the form of a long strip while remaining partially unvulcanized region in the vulcanization process, and such rubber-metal reinforcing material has to be vulcanized several times at least partly, to re-vulcanize after shaping into closed-end form by overlapping the unvulcanized regions. Therefore, the adherence property between rubber and reinforcing material in rubber crawler requires to have high resistance to heat such that it may be sustainable even when going through multiple times of the vulcanization. Further, it is preferable not to be degraded under high humidity which is often imposed when it is in use.

Here, the present invention intends to provide a rubber crawler with high durability due to the use of rubber composition, wherein said rubber composition exhibits enhanced adherence between rubber and metal reinforcing material, such as steel cord and the like, particularly adherence after heat aging and under high humidity, by not using vulcanizing retarder, such as CTP which may generate problems, such as blooming and lowering rubber physical properties after vulcanization; and by using vulcanization accelerator having an adequate vulcanization retarding effect that exert excellent working ability; lowering rubber scorching as much as possible.

Means for Solving the Problem

As a result of solving aforementioned problems, the inventors of the present invention found certain sulfenamide-containing vulcanization accelerators which result in the rubber crawler using the rubber composition that can exert high adhesion resistance to metal reinforcing material, as well as maintaining the adequate vulcanization retarding effect and excellent working ability, thus they completed the present invention. That is, the rubber crawler of the present invention is characterized in that the rubber composition used for the treatment rubber, which comprises in the amount of 0.1 to 10 parts by weight of sulfenamide-containing vulcanization accelerator represented by formula (I), 0.03 to 3 parts by weight of cobalt-containing composition as the equivalent amount of cobalt, and 0.3 to 10 parts by weight of sulfur, relative to 100 parts by weight of rubber component.

(Formula 1)

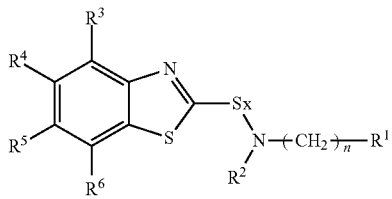

(I)

(In the above formula (I), $R^1$ is branched-alkyl group having from 3 to 12 carbon atoms; $R^2$ is straight-alkyl group having from 1 to 10 carbon atoms; $R^3$ to $R^6$ are hydrogen atom(s), straight-alkyl or alkoxy group having from 1 to 4 carbon atoms, or branched-alkyl or alkoxy group having from 3 to 4 carbon atoms, which may be the same or different; n is 0 or 1, and x is 1 or 2.)

In the above formula (I), $R^1$ may be tert-butyl group, $R^2$ may be straight-alkyl group having from 1 to 10 carbon atoms, n may be 0 or 1, and x is 1 or 2; $R^1$ is tert-butyl group, $R^2$ may be straight-alkyl group having from 1 to 4 carbon atoms, n may be 0.

Further, in the above formula (I), $R^3$ to $R^6$ may be all hydrogen atoms.

Moreover, the above rubber component preferably comprises at least one rubber component selected from the group consisting of natural rubber, polybutadien rubber, polyisoprene rubber and acrylicnitrile butadiene rubber.

Effect of the Invention

According to the present invention, the rubber composition using the vulcanization accelerator having the adequate vulcanization retarding effect for the treatment rubber is used, and in such rubber composition, the increase in Mooney viscosity is effectively inhibited, thus the kneading operation may be easier, together with maintaining preferable Mooney scorch time. In addition, such rubber composition does not require the use of vulcanizing retarder, such as CTP, which may generate problems, such as blooming and lowering rubber physical properties after vulcanization, so there is no possibility of exerting an adverse effect to appearance and adherence of the vulcanized rubber. Consequently, it is possible to obtain rubber composition exhibiting excellent working ability; lowering rubber scorching as much as possible, together with the enhanced adherence between rubber and metal reinforcing material after heat aging and under high humidity. Therefore, it is possible to attain the rubber crawler wherein high adherence durability between rubber and metal reinforcing material is maintained by using such rubber composition to the treatment rubber, even when being exposed to the extreme environment of production and of usage.

BRIEF DESCRIPTION OF THE DRAWINGS

FIG. 1 shows sectional view along width direction of one embodiment of the rubber crawler in this invention.

BEST MODE FOR CARRYING OUT THE INVENTION

The present invention is illustrated below.

The rubber crawler of the present invention comprises the use of rubber composition for the treatment rubber, wherein the rubber composition comprises in the amount of 0.1 to 10 parts by weight of sulfenamide represented by formula (I), 0.03 to 3 parts by weight of cobalt-containing composition as the equivalent amount of cobalt and 0.3 to 10 parts by weight of sulfur.

(Formula 2)

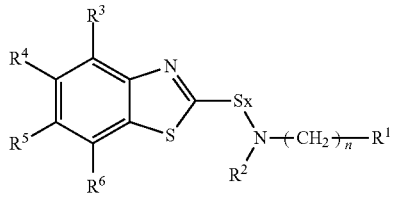

(I)

The rubber crawler of the present invention uses the rubber composition, comprising sulfenamide-containing vulcanization accelerator represented by the above formula (I), for the treatment rubber. Such sulfenamide-containing vulcanization has the adequate vulcanization retarding effect as well as effectively inhibiting the increase in its Mooney viscosity, together with the maintenance of preferable Mooney scorch time. Moreover, it is possible to exert excellent adherence resistance in the direct vulcanization adhesion of rubber composition with reinforcing material, such as steel cord, as well as exerting adherence that can sufficiently tolerate heat aging.

In sulfenamide-containing vulcanization accelerator represented by the above formula (I) of the present invention, $R^1$ is branched-alkyl group having from 3 to 12 carbon atoms. Accordingly, when $R^1$ is branched-alkyl having from 3 to 12 carbon atoms, vulcanization accelerator properties of the above sulfenamide-containing vulcanization accelerator is excellent, and the adhesion properties can be enhanced.

Particularly, $R^1$ includes isopropyl, isobutyl, triisobutyl, sec-butyl, tert-butyl, isoamyl(isopentyl), neopentyl, tert-amyl(tert-pentyl), isohexyl, tert-hexyl, isoheptyl, tert-heptyl, isooctyl, tert-octyl, isononyl, tert-nonyl, isodecyl, tert-decyl, isoundecyl, tert-undecyl, isododecyl, tert-dodecyl groups and the like. Of the above, tert-alkyl group is preferable, especially, tert-butyl, tert-amyl(tert-pentyl), tert-dodecyl, triisobutyl groups are preferable with respect to the effects such as preferable Moony scorch time. Of all, tert-butyl group is most preferable, because it exerts retention effect of vulcanization speed that is as same as that of sulfenamide-containing accelerator used for enhancing the adhesion and conventionally preferably used, in a well balance.

In sulfenamide-containing vulcanization accelerator represented in the above formula (I), n may be 0 or 1, and preferably 0 with respect to effects, such as easy synthesis and low cost in raw material. Moreover, in formula (I), x may be integer 1 or 2. When x is 3 or greater, the reactivity is too high, which may result in the decrease of the stability of sulfenamide-containing vulcanization accelerator and lowering of working ability.

It is presumed that when a bulky group is present proximal to —N— that is next to $R^1$, it tends to create a good Moony scorch time. Therefore, when $R^1$ is tert-butyl group and n is 0, relative to DCBS in which $R^1$ is cyclohexyl group and n is 0, the region proximal to —N— is more bulkier with the former one, and it is considered that more preferable Moony scorch time can be created. Further, in combination with $R^2$ described below, it is possible to exert preferable adhesion with preferable vulcanization speed in a good balance by the adequate regulation of having bulky substituent group in the position proximal to —N— and considering accumulation within human body.

In sulfenamide-containing vulcanization accelerator represented in the above formula (I) of the present invention, $R^2$ is straight-alkyl group having from 1 to 10 carbon atoms. If $R^2$ is branched-alkyl group, $R^1$ and $R^2$ are both branched-alkyl groups, it may not possess preferable stability when synthesized, and possibly decrease the heat resistance adherence. Particularly, when $R^1$ and $R^2$ are both tert-butyl groups, even its synthesis may be difficult. Therefore, when $R^2$ is straight-alkyl group having from 1 to 10 carbon atoms, its combination with $R^1$ having branched alkyl is excellent. Accordingly, it is possible to exert effective regulation of the bulkiness of substituent group positioned proximal to —N—, considering accumulation within human body and excellent adhesion property with preferable vulcanization speed.

In particular, $R^2$ includes methyl, ethyl, n-propyl, n-butyl, n-amyl(n-pentyl), n-hexyl, n-heptyl, n-octyl, nonyl, decyl, undecyl, dodecyl groups and the like. Of all, those having from 1 to 4 carbon atoms are preferable, having from 1 to 3 carbon atoms is more preferable, and having from 1 to 2 carbon atoms is most preferable, when considering the accumulation within human body by effectively regulating the bulkiness of substituent group positioned proximal to —N—.

Therefore, when sulfenamide-containing vulcanizing accelerator is such a current one wherein $R^2$ in the above formula (I) is H, the vulcanization speed may be too fast, thus it tends to not able to obtain excellent adhesion. Further, when $R^2$ is a bulky group, such as cyclohexyl group and long-chain group that is out of the above range, such as current sulfenamide-containing vulcanization accelerator, contradictorily the vulcanization speed tends to be too slow.

In particular, especially when $R^1$ is tert-butyl group and n is 0, methyl and ethyl are preferred for $R^2$, for obtaining both effects for enhancement of adhesion and maintaining vulcanization speed being as same as that of conventionally well-used sulfenamide-containing accelerator in a good balance, also considering the accumulation within human body.

In sulfenamide-containing vulcanization accelerator represented by the above formula (I), when $R^1$ is functional group besides branched-alkyl group having from 3 to 12 carbon atoms (for example, n-octadecyl group and the like) or branched-alkyl group having more than 12 carbon atoms; $R^2$ is functional group besides straight-alkyl group having from 1 to 10 carbon atoms (for example, n-octadecyl group and the like) or straight- or branched-alkyl group having more than 10 carbon atoms; and n is more than 2, the productivity and adhesion may decrease, or vulcanizing properties and rubber properties with the accelerator may decrease, due to slow Mooney scorch time to the extent outside the preferable range and may require long vulcanization time, thus it may not sufficiently exert intended effect of the present invention.

In the above formula (I), $R^3$ to $R^6$ may be hydrogen atoms, straight alkyl or alkoxy groups having from 1 to 4 carbon atoms, or branched-alkyl or alkoxy group having from 3 to 4 carbon atoms, which may be the same or different. Particularly, it is preferable for $R^3$ and $R^5$ to be straight-alkyl or alkoxy group having from 1 to 4 carbon atoms, or branched alkyl or alkoxy group having from 3 to 4 carbon atoms. Moreover, when $R^3$ to $R^6$ are alkyl or alkoxy group having from 1 to 4 carbon atoms, 1 carbon atom is preferable, and all $R^3$ to $R^6$ to be H is preferable. In any preferable case, it is desirable with respect easy synthesis of a compound and not delaying vulcanization speed. In the above formula (I), specific examples of $R^3$ to $R^6$ include methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, and tert-butoxy groups.

Further, as log Pow value (1-octanol/water partition coefficient) of the above sulfenamide-containing vulcanization accelerator are smaller, it is preferable with respect to ability to maintain the appropriate concentration. Particularly, as carbon atoms of $R^1$ and $R^2$ in the above formula (I) are smaller, the log Pow value tends to be smaller. For example, in the formula (I) used in the present invention, when $R^1$ is t-butyl and n is 0, then $R^2$ having 1 to 2 carbon atoms is preferable, because it shows both effects for enhancement of adhesion and maintaining vulcanization speed being as same as that of conventionally well-used sulfenamide-containing accelerator, in a good balance, as well as excellent adhesion, and it is also preferable with consideration of the accumulation within human body.

Moreover, log Pow value (1-octanol/water partition coefficient) is generally value that can be obtained from one of simplified assays evaluating the concentration of chemicals. Accordingly, it means a value that can be obtained in accordance with Pow which is the concentration ratio of a chemical in 2 phases when the chemical added to two solvent phases (1-octanol and water) is equilibrated The Pow is represented by below formula, and logarithmic value of Pow is log Pow value.

$$Pow=Co/Cw$$

Co: the concentration of tested agent in 1-octanol phase; and Cw: the concentration of tested agent in water phase.
According to JIS Z7260-117 (2006), log Pow value can be obtained by measuring Pow using high-performance liquid chromatography.

In the present invention, representative examples of sulfenamide-containing vulcanization accelerator represented by the above formula (I) include N-methyl-N-t-butylbenzothiazole-2-sulfenamide (BMBS), N-ethyl-N-t-butylbenzothiazole-2-sulfenamide (BEBS), N-n-propyl-N-t-butylbenzothiazole-2-sulfenamide, N-n-butyl-N-t-butylbenzothiazole-2-sulfenamide (BBBS), N-methyl-N-isoamylbenzothiazole-2-sulfenamide, N-ethyl-N-iso amylbenzothiazole-2-sulfenamide, N-n-propyl-N-isoamylbenzothiazole-2-sulfenamide, N-n-butyl-N-isoamylbenzothiazole-2-sulfenamide, N-methyl-N-tert-amylbenzothiazole-2-sulfenamide, N-ethyl-N-tert-amylbenzothiazole-2-sulfenamide, N-n-propyl-N-tert-amylbenzothiazole-2-sulfenamide, N-n-butyl-N-tert-amylbenzothiazole-2-sulfenamide, N-methyl-N-tert-heptylbenzothiazole-2-sulfenamide, N-ethyl-N-tert-heptylbenzothiazole-2-sulfenamide, N-n-propyl-N-tert-heptylbenzothiazole-2-sulfenamide, N-n-butyl-N-tert-heptylbenzothiazole-2-sulfenamide;

N-methyl-N-t-butyl-4-methylbenzothiazole-2-sulfenamide, N-methyl-N-t-butyl-4,6-dimethoxybenzothiazole-2-sulfenamide, N-ethyl-N-t-butyl-4-methylbenzothiazole-2-sulfenamide, N-ethyl-N-t-butyl-4,6-dimethoxybenzothiazole-2-sulfenamide, N-n-propyl-N-t-butyl-4-methylbenzothiazole-2-sulfenamide, N-n-propyl-N-t-butyl-4,6-dimethoxybenzothiazole-2-sulfenamide, N-n-butyl-N-t-butyl-4-methylbenzothiazole-2-sulfenamide, N-n-butyl-N-t-butyl-4,6-dimethoxybenzothiazole-2-sulfenamide, and the like. They may be used alone, or may be used in combination with 2 or more thereof.

Of all, N-methyl-N-t-butylbenzothiazole-2-sulfenamide (BMBS), N-ethyl-N-t-butylbenzothiazole-2-sulfenamide (BEBS), and N-n-propyl-N-t-butylbenzothiazole-2-sulfenamide are preferable with respect to enhanced adhesion properties.

Particularly, N-methyl-N-t-butylbenzothiazole-2-sulfenamide (BMBS) and N-ethyl-N-t-butylbenzothiazole-2-sulfenamide (BEBS) are preferable, and N-ethyl-N-t-butylbenzothiazole-2-sulfenamide (BEBS) is most preferable with respect to longest Mooney scorch time and excellent adhesion properties.

These sulfenamide-containing vulcanization accelerators can be used in combination with general vulcanization accelerators, such as N-tert-butyl-2-benzothiazolesulfenamide (TBBS), N-cyclohexyl-2-benzothiazolesulfenamide (CBS), dibenzothiazolyl disulfide (MBTS).

The content of the above sulfenamide-containing vulcanization accelerator is from 0.1 to 10 parts by weight, preferably from 0.1 to 0.7 parts by weight, more preferably from 0.1 to 0.6 parts by weight, relative to 100 parts by weight of the above rubber component. When the content of such vulcanization accelerator is less than 0.1 parts by weight, it may not vulcanize sufficiently, whereas when the content exceeds 100 parts by weight, it is easy to generate problems, such as blooming, cause rubber scorch, and lower the adhesion properties with reinforcing material.

A method for producing the above sulfenamide-containing vulcanization accelerator preferably includes the method below.

That is, N-chloroamine preliminarily prepared by reacting corresponding amine and sodium hypochlorite is reacted with bis(benzothiazol-2-yl)disulfide in an appropriate solvent in the presence of an amine and a base. When an amine is used as the base, the reacting solution obtained is neutralized, and then the free amine is isolated, which is followed by suitable post-treatments, such as filtration, washing, condensation and recrystallization, which are carried out depending on the properties of the solution, to obtain desired sulfenamide.

The base used in the present production process includes amine in excess, tertiary amines, such as triethyl amine, alkali hydroxides, alkali carbonates, alkali bicarbonates, sodium alkoxides and the like. Specifically, the method is preferred, in which an excess amine or triethylamine of a tertiary amine is used as the base to carry out the reaction, then the resulting hydrochloride salt is neutralized with sodium hydroxide to obtain desired compound, followed by recovering and reusing the amine from the filtrate.

The solvent used in the present production process is preferably alcohol, more preferably methanol.

For example, in N-ethyl-N-t-butylbenzothiazole-2-sulfonamide (BEBS), sodium hypochlorite was added dropwise to N-t-butylethylamine at temperature below 0° C., and was separated into two phases after stirring for 2 hours. Bis(benzothiazol-2-yl)disulfide, N-t-butylethylamine and said oil layer was suspended in methanol, and stirred for 2 hours under perfusion. The desired BEBS (white solid) was obtained after cooling, followed by neutralizing with sodium hydroxide, filtering, rinsing with water, and concentrating under reduced pressure, and re-crystallizing.

In the above rubber composition, it comprises the blend of cobalt-containing composition which largely contributes to enhancing initial adhesion properties. Such cobalt-containing compounds include organic cobalt salt, inorganic cobalt salt, such as cobalt chloride, cobalt nitrate, cobalt phosphate, cobalt chromate. Of all, organic cobalt salt is preferable with respect to further enhancing initial adhesion properties. They may be used alone, or may be used in combination with 2 or more thereof.

Particularly, cobalt salts of the above organic acids include at least one of cobalt naphthenate, cobalt stearate, cobalt neodecanoate, cobalt resinate, cobalt neodecanoate, cobalt versatate and tall oil fatty acid cobalt salt. In addition, the organic cobalt can be a complex salt having its part of the organic acid substituted with boric acid. In particular, trade name "MANOBOND®" commercially available from OMG, Inc. and the like can be used.

The content of the above cobalt-containing organic compound is in the amount of 0.01 to 3 parts by weight, preferably 0.03 to 0.06 parts by weight, relative to 100 parts by weight of the above rubber component. When the content of cobalt is less than 0.03 parts by weight, it may not enhance sufficient adhesion, whereas when the content exceeds 3 parts by weight, it may lower the heat-resistance after heat aging.

The above rubber composition is combined with sulfur as vulcanizing agent, besides the above component. Its content is in the amount of 0.3 to 10 parts by weight, preferably 1.0 to 7.0 parts by weight, more preferably 3.0 to 5.0 parts by weight, relative to 100 parts by weight of the above rubber component. When the content of sulfur is less than 0.3 parts by weight, it may not vulcanize sufficiently, whereas when the content exceeds 10 parts by weight, it may lower the rubber property after heat aging.

The rubber component of the above rubber composition is not specifically limited if it is rubber generally used for rubber articles, and can form sulfur bridge, if it is rubber component having double bond in a main chain, thus sulfonamide-containing vulcanization accelerator represented by the above formula (I) effectively functions, for example natural rubber or synthetic rubber can be used. Particularly, such synthetic rubber includes polybutadiene rubber, polyisoprene rubber, acrylonitrile-butadiene rubber, chloroprene rubber, styrene-butadiene rubber, ethylene-propylene-diene copolymer, halogenated butyl rubber, and the like. Of all, it is preferable to comprise at least one of natural rubber, polybutadiene rubber, polyisoprene rubber, acrylonitrile-butadiene rubber, with respect to adherence properties to the metal reinforcing material, such as steel cord, and the like. Further, it is more desirable to use natural rubber with respect to enhanced durability of the rubber crawler.

In the above rubber composition, additives besides the above component may be appropriately combined if necessary. Such additives includes, for example, vulcanizing agent besides the above sulfur, vulcanization accelerator or vulcanization accelerating aid besides above-mentioned vulcanization accelerator, or reinforcing fillers like carbon black, antioxidants, plasticizers, petroleum resins, waxes, oxidation inhibitors, oil, lubricants, ultraviolet absorbing agents, dispersing agents, compatibilizers, homogenizing agents, and the like. Such rubber composition can be produced from each of the above components by kneading them together, for example, with a Banbury mixer or a kneader.

The rubber crawler of the present invention uses the above rubber composition as the treatment rubber. The structure of such rubber crawler is produced by coating steel cord (2), which is reinforcing material, with treatment rubber (1) as shown in the sectional view along width direction (FIG. 1), and a part of core (5) comprising disengagement preventing projections (3) and wing portions (4) on its inner peripheral side, is embedded in a rubber member (7) having lags (6) formed on the mounting surface side.

The method for producing such rubber crawler is illustrated as follows.

First, the inner rubber sheet (the rubber member (7)) is spread in the bottom mold, which compartmentalize inner peripheral side of the rubber crawler; the core (5) is arranged on top and then a rubber sheet and the treatment rubber (1) are arranged in order; and the steel cord (2) is positioned to be bound in the form of line on the top. This is followed by arranging the treatment rubber (1) and the outer rubber sheet (the rubber member 7) in order, closing the upper mold, which compartmentalizes the outer peripheral side of the rubber crawler, and vulcanizing-and-molding the rubber composition. Generally, in this vulcanization formation, in order to shape into the closed-end form from a long strip, such rubber-metal reinforcing material is left unvulcanized at least partly, and such parts positioned in the center are overlapped; then they are re-vulcanized to obtain the rubber crawler.

Moreover, tin coating steel cord, brass coating steel cord, and the like may be used as the above steel cord (2). In addition, the composition as same as the rubber composition of treatment rubber (1) may be used as the rubber composition forming the above rubber member (7). In this case, it is necessary to arbitrarily select the thickness of the treatment rubber (1) by considering the thickness formed from rubber member (7).

EXAMPLE

The following specifically illustrates the present invention based on Examples, but these examples are not limiting the scope of the invention.

Further, values of log Pow can be obtained by measuring Pow using high-performance liquid chromatography, according to JIS Z7260-117 (2006).

Preparation 1

Synthesis of
N-ethyl-N-t-butylbenzothiazole-2-sulfenamide
(vulcanization accelerator 1)

148 g of 12% sodium hypochlorite was added to 16.4 g (0.162 mol) of N-t-butylethylamine at the temperature below 0° C., and then the oil phase of separated two phases was obtained after stirring for two hours. Accordingly, 39.8 g (0.120 mol) of bis(benzothiazole-2-yl)disulfide, 24.3 g (0.240 mmol) of N-t-butylmethylamine and the oil phase above were suspended in 120 mL of methanol, and the mixture was stirred for 2 hours under perfusion. After cooling, it was neutralized with sodium hydroxide, then the filtering, rinsing with water, condensing under reduced pressure were performed, which is followed by re-crystallization, to obtain 41.9 g (yield of 66%) of desired vulcanization accelerator 1 as white solid (melting point 60 to 61° C., log Pow value 4.9)

A spectrum data for the vulcanization accelerator 1 obtained is shown below.

$^1$H-NMR (400 MHz, CDCl$_3$) δ=1.29 (t, 3H, J=7.1 Hz, CH$_3$(ethyl)), 1.34 (s, 9H, CH$_3$(t-butyl)), 2.9-3.4 (br-d, CH$_2$), 7.23 (1H, m), 7.37 (1H, m), 7.75 (1H, m), 7.78 (1H, m).

$^{13}$C-NMR (100 MHz, CDCl$_3$) δ=15.12, 28.06, 47.08, 60.41, 120.70, 121.26, 123.23, 125.64, 134.75, 154.93, 182.63.

Mass analysis (EI, 70 eV): m/z; 251 (M$^+$-CH$_4$), 167 (M$^+$-C$_6$H$_{14}$N), 100 (M$^+$-C$_7$H$_5$NS$_2$): IR (KBr, cm$^{-1}$): 3061, 2975, 2932, 2868, 1461, 1429, 1393, 1366, 1352, 1309, 1273, 1238, 1198, 1103, 1022, 1011, 936, 895, 756, 727.

Preparation 2

Synthesis of
N-methyl-N-t-butylbenzothiazole-2-sulfenamide
(BEBS, vulcanization accelerator 2)

The same procedure as Preparation 1 is performed using 14.1 g (0.162 mol) of N-t-butylmethylamine in place of N-t-butylethylamine, to obtain the vulcanization accelerator 2 as white solid (melting point 56 to 58° C., log Pow value 4.5).

A spectrum data for the vulcanization accelerator 2 obtained is shown below.

$^1$H-NMR (400 MHz, CDCl$_3$) δ=1.32 (9H, s, CH$_3$(t-butyl)), 3.02 (3H, s, CH$_3$(methyl)), 7.24 (1H, m), 7.38 (1H, m), 7.77 (1H, m), 7.79 (1H, m).

$^{13}$C-NMR (100 MHz, CDCl$_3$) δ=27.3, 41.9, 59.2, 120.9, 121.4, 123.3, 125.7, 135.0, 155.5, 180.8.

Mass analysis (EI, 70 eV) m/z; 252 (M$^+$), 237 (M$^+$-CH$_3$), 223 (M$^+$-C$_2$H$_6$), 195 (M$^+$-C$_4$H$_9$), 167 (M$^+$-C$_5$H$_{12}$N), 86 (M$^+$-C$_7$H$_4$NS$_2$).

Preparation 3

Synthesis of
N-n-propyl-N-t-butylbenzothiazole-2-sulfenamide
(vulcanization accelerator 3)

The same procedure as Preparation 1 is performed using 18.7 g (0.162 mol) of N-n-propyl-t-butylamine in place of N-t-butylmethylamine, to obtain the vulcanization accelerator 3 as white solid (melting point 50 to 52° C., log Pow value5.3).

$^1$H-NMR (400 MHz, CDCl$_3$) δ=0.92 (t, J=7.3 Hz, 3H), 1.34 (s, 9H), 1.75 (br, 2H), 3.03 (brd, 2H), 7.24 (t, J=7.0 Hz, 1H), 7.38 (t, J=7.0 Hz, 1H), 7.77 (d, J=7.5 Hz, 1H), 7.79 (d, J=7.5 Hz, 1H).

$^{13}$C-NMR (100 MHz, CDCl$_3$) δ=11.7, 23.0, 28.1, 55.3, 60.4, 120.7, 121.3, 123.3, 125.7, 134.7, 154.8, 181.3.

Comparative Preparation 1

Synthesis of
N-i-propyl-N-t-butylbenzothiazole-2-sulfenamide
(vulcanization accelerator 4)

The same procedure as Preparation 1 is performed using 18.7 g (0.162 mol) of N-i-propyl-t-butylamine in place of N-t-butylmethylamine, to obtain the vulcanization accelerator 4 as white solid (melting point 68 to 70° C.).

$^1$H-NMR (400 MHz, CDCl$_3$) δ=1.20-1.25 (dd, (1.22 ppm: J=6.4 Hz, 1.23 ppm: J=6.4 Hz) 6H), 1.37 (s, 9H), 3.78 (m, J=6.3 Hz, 1H), 7.23 (t, J=7.0 Hz, 1H), 7.38 (t, J=7.0 Hz, 1H), 7.77 (d, J=7.5 Hz, 1H), 7.79 (d, J=7.5 Hz, 1H).

$^{13}$C-NMR (100 MHz, CDCl$_3$) δ=22.3, 23.9, 29.1, 50.6, 61.4, 120.6, 121.2, 123.2, 125.6, 134.5, 154.5, 183.3.

Examples 1 to 4

Comparative Examples 1 to 3

A 2200 mL of Banbury mixer was used to knead and mix the rubber component, the vulcanization accelerator and other additives in the composition formula according to Table 1, to obtain the unvulcanized rubber composition. Accordingly, Moony viscosity and Moony scorch time were measured according to methods below, and the tension evaluation and adhesion durability evaluation against heat and humidity were performed and evaluated according to methods below. The results are shown in Table 1.

<<Mooney Viscosity and Mooney Scorch Time>>

The evaluations were carried out according to JIS K 6300-1:2001.

In the evaluations, values for Comparative Example 1 were set to 100. In Mooney viscosity, a smaller value shows that the working ability at the time of kneading is more favorable. In Mooney scorch time, a larger value shows that the working ability at the time of kneading is more favorable.

<<Tension Evaluation>>

JIS dumbbell No. 3 test sample consisting of the rubber composition obtained was prepared, and it was measured for the tensile strength at break (Tb), the elongation at break (Eb), the stress at 100% elongation (M100) in accordance with JIS K 6251:2004 of elongating evaluation at 25° C. Each value for the rubber composition of Comparative Example 1 is shown individually as the index display of 100. In the index value, larger index value indicates higher break-resistance.

<<Adhesion Durability Evaluation Against Heat and Humidity>>

A sheet (thickness of 15 mm) consisting of obtained rubber composition was prepared by intervening steel cord (diameter of 7 mm) in between a pair of sheets, then was vulcanized under increased pressure for 40 minutes to prepare the test specimen.

The steel cord was pulled out from each test specimen after leaving the above sample specimen in the bath of constant temperature and constant humidity of the temperature of 40° C. and relative humidity of 95% for 21 days and 35 days. Accordingly, conditions of rubber coating on the steel cords were visually observed and were indicated from 0 to 100% for the index of adhesion evaluation against heat and humidity. In index of adhesion against heat and humidity, larger values show more excellent adhesion against heat and humidity.

<<Durability Evaluation of the Rubber Crawler>>

In the deterioration accelerating evaluation (the deteriorating speed was 20-30 fold of that of commercially available) at the time of the actual crawler traveling, the time when adhesion-peeling of the rubber from the steel cord started at the overlapping region was measured. The body in size of 2.5 to 5 t was used, and the width of rubber crawler was from 300 to 600 mm. The values for Comparative Example 1 were set to 100. A larger value shows more excellent durability as a rubber crawler.

As is apparent from the results of Table 1, Examples 1 to 4, comprising rubber component, a certain amount of cobalt-containing compound and vulcanization accelerator specified above, maintained favorable working ability while inhibiting the decrease in the elongation at break (Eb), the tensile strength at break (Tb) and the stress at 100% elongation (M100), and preventing the decrease in break-resistance, and comprising durability as rubber crawler with excellent adhesion evaluation against heat and humidity, relative to Comparative Example 1 to 3 comprising current vulcanization accelerator. It is apparent that such adhesion evaluation against heat and humidity can obtain more significant effect, especially in a long-term. According to Example 4, the same effect can be obtained when combining said particular vulcanization accelerator and current vulcanization accelerator.

DESCRIPTION OF NUMERALS

1: Treatment rubber
2: Steel cord
3: Disengagement preventing projections
4: Wing portions
5: Core
6: Lag
7: Rubber member

The invention claimed is:

1. A rubber crawler characterized in that said rubber crawler comprises a rubber composition used as a treatment rubber thereof, which comprises 0.1 to 0.6 parts by weight of sulfenamide-containing vulcanization accelerator represented by formula (I), 0.03 to 3 parts by weight of cobalt-containing composition as the equivalent amount of cobalt and 0.3 to 10 parts by weight of sulfur, relative to 100 parts by weight of rubber component;

TABLE 1

|  | Comparative Example 1 | Comparative Example 2 | Comparative Example 3 | Example 1 | Example 2 | Example 3 | Example 4 |
|---|---|---|---|---|---|---|---|
| Natural rubber | 100 | 100 | 100 | 100 | 100 | 100 | 100 |
| HAF carbon black*[1] | 50 | 50 | 50 | 50 | 50 | 50 | 50 |
| Antioxidant*[2] | 0.5 | 0.5 | 0.5 | 0.5 | 0.5 | 0.5 | 0.5 |
| Cobalt versatate*[3] | 1 | 1 | 1 | 1 | 1 | 1 | 1 |
| Zinc oxide*[4] | 4 | 4 | 4 | 4 | 4 | 4 | 4 |
| Sulfur*[5] | 5 | 5 | 5 | 5 | 5 | 5 | 5 |
| Vulcanization accelerator A*[6] | 0.6 | | | | | | |
| Vulcanization accelerator A*[7] | | 0.6 | | | | | 0.2 |
| Vulcanization accelerator 1 | | | | 0.6 | | | 0.4 |
| Vulcanization accelerator 2 | | | | | 0.6 | | |
| Vulcanization accelerator 3 | | | | | | 0.6 | |
| Vulcanization accelerator 4 | | | 0.6 | | | | |
| Assessment | 100 | 99 | 95 | 97 | 95 | 95 | 98 |
| Mooney viscosity ($ML_{1+4}$) | 100 | 113 | 115 | 125 | 105 | 110 | 118 |
| Mooney scroch time (ts) | 100 | 107 | 100 | 104 | 98 | 96 | 104 |
| Tension evaluation    Tb | 100 | 110 | 102 | 106 | 104 | 100 | 101 |
| Eb | 100 | 100 | 98 | 102 | 102 | 101 | 100 |
| Adhesion evaluation against    Day 21 | 80 | 80 | 85 | 100 | 95 | 90 | 85 |
| heat and humidity    Day 35 | 0 | 0 | 25 | 45 | 45 | 40 | 25 |
| Durability evaluation of rubber crawler | 100 | 95 | 120 | 160 | 145 | 145 | 120 |

The unit for values of each component in the rubber composition is parts by weight.
*[1]#70-NP, manufactured by Asahi Carbon, Co., Ltd.
*[2]ANTIGENE6C, manufactured by Sumitomo Chemical, Co., Ltd.
*[3]Cobalt versatate, the amount of cobalt: 14% w/w manufactured by Dainippon Ink and Chemicals, Inc.
*[4]Ginrei SR, manufactured by Toho Zinc Co., Ltd.
*[5]Sulfax 5, Tsurumi Chemical Industry Co., Ltd.
*[6]N-cyclohexyl-2-benzotohiazol sulfenamide (Noccellar CZ, manufactured by Ouchi Shinko Chemical Industrial)
*[7]N-t-butylbenzothiazol-2-sulfenamide (Noccellar NS, manufactured by Ouchi Shinko Chemical Industrial)

[Formula 1]

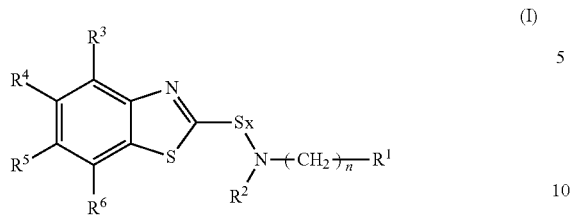

(wherein $R^1$ is branched-alkyl group having from 3 to 12 carbon atoms; $R^2$ is straight-alkyl group having from 1 to 10 carbon atoms; $R^3$ to $R^6$ are hydrogen atom(s), straight-alkyl or alkoxy group having from 1 to 4 carbon atoms, or branched-alkyl group or alkoxy group having from 3 to 4 carbon atoms, which may be the same or different; n is 0 or 1; and x is 1 or 2).

2. A rubber crawler according to claim 1, wherein $R^1$ is tert-butyl group; $R^2$ is straight-alkyl group having from 1 to 6 carbon atoms; and n is 0, in the above formula (I).

3. A rubber crawler according to claim 1, wherein $R^1$ is tert-butyl group; $R^2$ is straight-alkyl group having from 1 to 4 carbon atoms; and n is 0, in the above formula (I).

4. A rubber crawler according to claim 1, wherein $R^3$ to $R^6$ are all hydrogen atoms.

5. A rubber crawler according to claim 1, wherein said rubber component comprises at least one selected from the group consisting of natural rubber, polybutadiene rubber, polyisoprene rubber, and acrylonitrile-butadiene rubber.

\* \* \* \* \*